United States Patent
Blaha

(10) Patent No.: US 10,172,966 B2
(45) Date of Patent: Jan. 8, 2019

(54) IMAGE GUIDED BORONATED GLUCOSE NEUTRON CAPTURE THERAPY

(71) Applicant: Charles Blaha, San Francisco, CA (US)

(72) Inventor: Charles Blaha, San Francisco, CA (US)

(*) Notice: Subject to any disclaimer, the term of this patent is extended or adjusted under 35 U.S.C. 154(b) by 460 days.

(21) Appl. No.: 14/959,963

(22) Filed: Dec. 4, 2015

(65) Prior Publication Data

US 2016/0158391 A1 Jun. 9, 2016

Related U.S. Application Data

(60) Provisional application No. 62/087,538, filed on Dec. 4, 2014.

(51) Int. Cl.
*A61K 41/00* (2006.01)
*A61K 51/04* (2006.01)

(52) U.S. Cl.
CPC ...... *A61K 51/0491* (2013.01); *A61K 41/0095* (2013.01)

(58) Field of Classification Search
None
See application file for complete search history.

(56) References Cited

U.S. PATENT DOCUMENTS 5,466,679 A * 11/1995 Soloway ............... C07H 19/06
424/1.11
2008/0050309 A1 2/2008 Witczak et al.

OTHER PUBLICATIONS

Wang et al. Evaluation of F-18-labeled amino acid derivatives and [18F]FDG as PET probes in a brain tumor-bearing animal model. 2005 Nucl. Med. Biol. 32: 367-375. (Year: 2005).*
Kabalka et al. Evaluation of fluorine-18-BPA-fructose for boron neutron capture treatment planning. 1997 J. Nucl. Med. 38: 1762-1777. (Year: 1997).*
Videtic, "Locally advanced non-small cell lung cancer: what is the optimal concurrent chemoradiation regimen?" Cleveland Clinic Journal of Medicine, May 2012, pp. e-S32-e-S37, vol. 79, Supp. 1.
Akan, "Boron neutron capture therapy for breast cancer," International Journal of Women's Health and Reproduction Sciences, Apr. 2015, vol. 3, No. 2 (1 page).
Akan et al., "Complexion of boric acid with 2-deoxy-d-glucose (DG) as a novel boron carrier for BNCT," Medical Science and Discovery, Oct. 2014, pp. 65-71, vol. 1, No. 3.
Akan et al., "Genotoxicity and cytotoxicity of novel 10B carrier ((2R)-4,5,6-trihydroxy-2-2(hydroxymethyl)tetrahydro-2hpyran-3-yl)boronic acid)," Medical Science and Discovery, Dec. 2014, pp. 96-108, vol. 1, No. 4.
Barth et al., "Current status of boron neutron capture therapy of high grade gliomas and recurrent head and neck cancer," Radiation Oncology, 2012, pp. 1-21, vol. 7, No. 146.
Ben-Haim et al., "18F-FDG PET and PET/CT in the evaluation of cancer treatment response," Journal of Nuclear Medicine, Jan. 2009, pp. 88-99, vol. 50, No. 1.
Choi et al., "Potential of 18F-FDG PET toward personalized radiotherapy or chemoradiotherapy in lung cancer," European Journal of Nuclear Medicine and Molecular Imaging, Jun. 2013, pp. 832-841, vol. 40.
Danielsen et al., "Positron emission tomography in the follow-up of cutaneous malignant melanoma patients: a systematic review," American Journal of Nuclear Medicine and Molecular Imaging, 2014, pp. 17-28, vol. 4, No. 1.
Dibble et al., "PET/CT of cancer patients: part 1, pancreatic neoplasms," American Journal of Roentgenology, Nov. 2012, pp. 952-967, vol. 199.
Ferda et al., "18F-FDG-PET/CT in potentially advanced renal cell carcinoma: a role in treatment decisions and prognosis estimation," Anticancer Research, Jun. 2013, pp. 2665-2672, vol. 33.
Groheux et al., "Prognostic impact of (18)FDG-PET-CT findings in clinical stage III and IIB breast cancer," Journal of the National Cancer Institute, Dec. 19, 2012, pp. 1879-1887, vol. 104, Issue P.
Hellwig et al., "Value of F-18-fluorodeoxyglucose positron emission tomography after induction therapy of locally advanced bronchogenic carcinoma," Journal of Thoracic and Cardiovascular Surgery, Dec. 2004, pp. 892-899, vol. 128, No. 6.
Jadvar, "Imaging evaluation of prostate cancer with 18F-fluorodeoxyglucose PET/CT: utility and limitations," European Journal of Nuclear Medicine and Molecular Imaging, Jul. 2013, pp. 5-10, vol. 40, No. 1.
Jadvar, "Molecular Imaging of Prostate Cancer with PET," Journal of Nuclear Medicine, Oct. 2013, pp. 1685-1688, vol. 54, No. 10.
Kostakoglu et al., "State-of-the-Art Research on Lymphomas: Role of Molecular Imaging for Staging, Prognostic Evaluation, and Treatment Response," Frontiers in Oncology, Sep. 4, 2013, pp. 1-9, vol. 3, Article 212.
Molina et al., "Non-small cell lung cancer: epidemiology, risk factors, treatment, and survivorship," Mayo Clinic Proceedings, May 2008, pp. 584-594, vol. 83, No. 5.
Ozkan, "Positron emission tomography/computed tomography in locally advanced breast cancer," Experimental Oncology, Dec. 2013, pp. 253-257, vol. 35, No. 4.
Patel et al., "18F-FDG PET/CT of cervical carcinoma," American Journal of Roentgenology, May 2011, pp. 1225-1233, vol. 196.
Tjarks et al., Synthesis and in Vitro Evaluation of Boronated Uridine and Glucose Derivatives for Boron Neutron Capture Therapy, J. Med. Chem., 1992, pp. 1628-1633, vol. 35, No. 9.
Williams et al., "Suppression of Myocardial 18F-FDG Uptake by Preparing Patients with a High-Fat, Low-Carbohydrate Diet," Nuclear Medicine, Feb. 2008, pp. W151-W156, vol. 190, No. 2.
Yalcin, "Overview on locally advanced breast cancer: defining, epidemiology, and overview on neoadjuvant therapy," Experimental Oncology, Dec. 2013, pp. 250-252, vol. 35, No. 4.

(Continued)

*Primary Examiner* — Michael G. Hartley
*Assistant Examiner* — Jennifer Lamberski
(74) *Attorney, Agent, or Firm* — Dorsey & Whitney LLP

(57) ABSTRACT

Disclosed herein are methods, processes, devices, and compositions for the treatment of target cells and/or tissues, the treatment comprising identifying the target cell with positron emission tomography and then directing a epithermal neutron toward the identified target cell. In various aspects, the target cells and/or tissues take up and metabolize boronated glucose and radioactive fluorinated glucose molecules.

12 Claims, No Drawings

(56) References Cited

OTHER PUBLICATIONS

Tsutani et al., "Prognostic significance of metabolic response by positron emission tomography after neoadjuvant chemotherapy for resectable malignant pleural mesothelioma," Annals of Oncology, Apr. 2013, pp. 1005-1010, vol. 24, No. 4.
Mertens et al., "Detecting primary bladder cancer using delayed (18)F-2-fluoro-2-deoxy-D-glucose-positron emission tomography/computed tomography imaging after forced diuresis," Indian Journal of Nuclear Medicine, Jul.-Sep. 2012, pp. 145-150, vol. 27, No. 3.
Govindan et al., "Locally advanced non-small cell lung cancer: the past, present, and future," Journal of Thoracic Oncology, Aug. 2008, pp. 917-928, vol. 3, No. 8.
Massaccesi et al., "$^{18}$F-FDG PET-CT during chemo-radiotherapy in patients with non-small cell lung cancer: the early metabolic response correlates with the delivered radiation dose," Radiation Oncology, 2012, pp. 1-10, vol. 7, No. 106.

\* cited by examiner

IMAGE GUIDED BORONATED GLUCOSE NEUTRON CAPTURE THERAPY

CROSS REFERENCE TO RELATED APPLICATIONS

This application claims the benefit under 35 U.S.C. § 119(e)(1) of U.S. Provisional Patent Application No. 62/087,538 filed on Dec. 4, 2014, the contents of which are hereby expressly incorporated by reference herein, for all purposes.

FIELD

The presently claimed methods, processes, and compositions are directed to the imaging, diagnosis, and treatment of tissues having rapidly growing or more metabolically active cells, which can include cancerous and non-cancerous cells.

BACKGROUND

Each year, in the U.S. alone, over 1.5 million people are diagnosed with cancer and approximately 600,000 people die of cancer. Numerous cancer therapeutics presently exist, however many of the known therapeutics are unable to treat and cure a significant number of cancer cases because they do not adequately target and destroy cancer cells.

Diagnosing cancer is an extremely important clinical practice. A large and growing number of cancer cases are diagnosed and monitored via positron emission tomography (PET) scans. PET scans consist of injecting a radiolabeled fluorinated glucose analog (FDG) into a patient and then detecting positrons emitted during radioactive decay of the FDG. Since FDG is structurally similar to glucose, it is internalized by the patient's cells in the same manner as glucose. The emitted positrons are detected and the emission pattern processed to produce an image. This image allows the location of the FDG in the patient to be determined.

PET is a powerful imaging method in the diagnosis of cancer because at least two-thirds (about 66%) of cancers exhibit an increased glucose metabolism in comparison to normal tissue. These cancers therefore internalize and metabolize FDG at a higher rate than other, non-cancerous tissues. As a result, the cancerous tissue shows a greater concentration of FDG than other, non-cancerous cells in a PET scan. The increased concentration of FDG in cancer tissue is seen as "hot spots," or darker shaded images than normal tissue, on the PET scan.

PET scans can have a resolution of a few millimeters and may be quantitative. Therefore, small amounts of tissue can be resolved, and the quantitative rate of glucose metabolism in that small amount of tissue, can be determined.

In the 1950's Boron Neutron Capture Therapy (BNCT) was developed as a cancer therapeutic and tested in clinical trials. BNCT consists of injecting a boron-containing molecule into a patient that is then internalized by cancerous cells at a significantly greater rate than non-cancerous cells. The boron-containing molecule should therefore accumulate in cancerous cells. After a sufficient concentration difference of the boronated molecule has been achieved between the cancerous tissue and the neighboring non-cancerous tissue, the region of interest, which includes the cancerous tissue, is exposed to a beam of epithermal neutrons. Epithermal neutrons are low energy neutrons that penetrate and minimally interact with body tissue. However, epithermal neutrons strongly interact with boron. When an epithermal neutron collides with a boron atom, it yields a radioactive alpha particle—a highly biologically toxic form of ionizing radiation. Thus, when a boron molecule is located within a cell and an epithermal neutron collides with it, the released alpha particle may lead to cell damage, including death.

Clinical trials have been performed to investigate two potential boron-carrier molecules for BNCT: boronophenylalanine (boronated phenylalanine or BPA) and mercaptoundecahydrododecaborate (sodium borocaptate or BSH). Neither of these molecules, BPA nor BSH, is approved for routine clinical use. In part, this failure to be approved may have been due to the fact that neither molecule preferentially accumulates in cancer cells in sufficient amounts to distinguish the cancer tissue from normal tissue. Without sufficient accumulation, there will be little or no preferential targeting of cancer tissue by exposure to epithermal neutrons.

Another drawback of BNCT is that the absolute concentration of BPA or BSH in the cells of the patient cannot be measured or determined at the time of treatment (i.e., when the patient is exposed to a beam of epithermal neutrons). A healthcare provider, therefore, has no way of knowing whether a therapeutic level of boron has accumulated within the cancerous tissue. Likewise, the healthcare provider cannot be assured that a non-therapeutic level of boron exists in neighboring, non-cancerous tissue.

There is thus a need for improved targeting molecules that will enhance the effectiveness of BNCT. There is also a need for more accurate determination of the amount of the boron-carrying molecule located within the cancerous tissue and neighboring, non-cancerous tissue.

SUMMARY

Disclosed herein are therapeutic compounds for targeting and destroying cancer cells, or other cells displaying an increased or heightened level of glucose metabolism as compared to normal cells, as well as methods of using the therapeutic compounds. The disclosed therapeutic compounds allow a healthcare provider to visualize the treatment site prior to administering treatment. In one embodiment, a composition for the treatment of a cellular disorder is disclosed. The composition comprises fluorinated glucose, boronated glucose and a pharmaceutically acceptable vehicle, adjuvant, or excipient. In some embodiments, the fluorinated glucose and the boronated glucose are formulated for uptake into one or more cells and the boronated glucose is formulated for contact with epithermal neutrons subsequent to the uptake into the one or more cells. In some embodiments, the cellular disorder is cancer, for example non-small cell lung cancer or small cell lung cancer.

In some embodiments, the boronated glucose is a compound of Formula (IV):

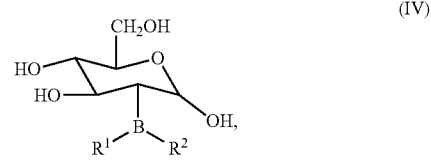

(IV)

wherein R1 and R2 are independently selected from H, —OH and $C_{1-4}$ alkyl. As used herein, "$C_{1-4}$ alkyl" refers to a saturated or unsaturated, branched, or straight-chain, monovalent hydrocarbon radical derived by the removal of one hydrogen atom from a single carbon atom of a parent alkane, alkene, or alkyne. Examples of $C_{1-4}$ alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; and butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.

Also disclosed herein are methods of treating a cellular disorder, comprising administering fluorinated glucose to a subject, administering boronated glucose to the subject, performing a PET scan of the subject, identifying the locations of a target tissue from the PET scan, and contacting the boronated glucose localized within the target tissue with epithermal neutrons, wherein the fluorinated glucose and the boronated glucose co-localize to the same location in the subject. In many embodiments of the disclosed method, the fluorinated glucose is administrated prior to, or subsequent to the boronated glucose. In some embodiments, the fluorinated glucose and the boronated glucose are administered at the same time. In some embodiments, the fluorinated glucose and the boronated glucose are administered together.

DETAILED DESCRIPTION

The present disclosure is based on the surprising discovery that fluorinated glucose and boronated glucose may be administered to a patient at or near the same point in time. In some cases the modified glucoses will be metabolized similarly by cells. For example, both fluorinated and boronated glucose will be taken up by cells. When administered at or about the same time, the fluorinated glucose may be used to help to identify tissues having rapidly growing or more metabolically active cells. In these embodiments, rapidly growing cells take up more fluorinated glucose than other cells. These cells may therefore be identified by PET analysis because they may accumulate more fluorinated glucose than other cells. Because the boronated glucose is metabolized similarly to fluorinated glucose, cells accumulating fluorinated glucose will also accumulate boronated glucose. Accumulation of boronated glucose may aid in treating cells within a tissue that has accumulated fluorinated glucose, using BNC Therapy. Thus, in various aspects, fluorinated and boronated glucose are provided to a patient at or about the same time, the uptake of modified glucose by the rapidly growing or more metabolically active cells is followed using PET of the fluorinated glucose, and then the metabolically active or rapidly growing cells identified by the PET scan are contacted with a beam of epithermal neutrons.

The disclosed treatment methods and related protocols offer an effective means of treating a broad spectrum of cellular disorders, including, without limitation, cellular proliferative disorders, solid cancers and non-solid cancers, among others. The methods, processes, devices, and compounds of the present disclosure may allow healthcare providers to visualize diseased or otherwise unusually metabolically active target cells, quantify the amount of therapeutic compound accumulated within those cells, and selectivity target those cells for treatment with epithermal neutrons. The present disclosure provides methods that advantageously aid in optimizing the therapeutic potential of epithermal neutrons directed at a diseased or unusually metabolically active tissue or cell. In part, this may be accomplished through adjustment of the concentrations of boronated glucose and/or the ratio of fluorinated to boronated glucose. In many embodiments, the disclosed methods, processes, devices and compounds aid in preferentially targeting or selecting a cell that is rapidly growing and/or that is more metabolically active than normal cells within a normal tissue. In some embodiments, the preferentially targeted or selected cell is cancerous.

The present disclosure is based, in part, on the surprising discovery that cells are able to internalize and metabolize boronated glucose. In some cases, boronated glucose is internalized and metabolized similarly to non-boronated glucose and/or fluorinated glucose. Certain cells internalize and metabolize glucose at a higher rate than other cells. In some embodiments those cells may be rapidly growing cells or cells that are more metabolically active than other cells. In some embodiments, cells that internalize and metabolize glucose at a higher rate may be cancerous cells. Cells that internalize and metabolize glucose at a higher rate than other cells also internalize and metabolize modified glucose at a higher rate than other cells. In some embodiments the modified glucose may be fluorinated or boronated glucose. In the case of boronated glucose, such cells internalize and accumulate more boron within themselves than other cells internalize, resulting in a difference in boron concentration between cells with a higher metabolic rate and cells with a normal level of cellular metabolism. The result being a higher concentration of boron in the cells with a higher metabolic rate as compared to the cells with a lower or normal metabolic rate. When epithermal neutrons are directed at cells containing boron, the collision of the epithermal neutron and boron generates alpha particles. Cells with higher accumulation of boron than other cells will be exposed to greater amounts of alpha particles than other cells, and will accumulate more damage from exposure to alpha particle than other cells. When the concentration of boron in a cell is high enough, the amount of alpha particles generated during neutron collisions causes sufficient damage to kill the cell. In that respect, the methods, processes, devices, and compounds of the present disclosure can be used to selectively kill rapidly growing cells or cells that are more metabolically active than other cells.

Positron Emission Tomography:

Positron Emission Tomography (PET) is an imaging technique used to diagnose various medical conditions including cancer and cardiovascular disease. In many embodiments, PET may use a radiolabeled drug, which admits radiation, and a radiation capturing scanner. The most commonly used radiolabeled drug is fluorinated glucose, or 18F-2-fluoro-2-deoxy-D-glucose (FDG), which contains a radioactive fluorine atom that decays and gives off radiation, or more specifically a positron. FDG is a glucose analog that is typically administered to a patient by intravenous injection. After injection FDG is internalized and/or metabolized by the patient's cells. As described herein, in many cases, FDG accumulates to a greater degree in cells and tissues that have high metabolic activity and/or are rapidly growing and/or dividing. These tissues and cells have a higher need for glucose uptake in order to compensate for their heightened metabolic activity and/or rapid rate of growth and division. Such cells do not differentiate between FDG and glucose, and will thus take in FDG as if it were unmodified glucose. Tissues with high concentrations of FDG release greater amounts of radiation (or positrons) than other tissues with lower concentrations of FDG. These differences in radiation emissions are detected by the PET scanner.

PET scanners use image processing software to locate and map the patient's tissues displaying high positron emissions. These maps may aid in the diagnosis, monitoring, and treatment of disease, for example, without limitation, cancer.

In some embodiments, PET analysis may be combined with x-ray computed tomography (CT-scan). In these embodiments, a CT-scan and PET scan combine to provide anatomical information and a reference frame for more precise location of high positron-emitting tissues.

In some embodiments, PET may be qualitative, semi-quantitative, and/or quantitative. In some embodiments, quantitative PET can be further sub-categorized by the kinetic model used in the analysis. In some embodiments, qualitative PET scans provide visual analysis of the image readouts from the PET scan via imaging reconstruction software. The region of interest—the region displaying enhanced positron emission as compared to other tissues, thus indicating a greater accumulation of FDG—is qualitatively compared to surrounding tissue to determine the degree of difference in FDG uptake. This method may, in some cases, be affected by numerous factors including blood glucose levels, insulin levels, the rate of FDG uptake by the surrounding tissue(s) and the amount of time between the injection of FDG and the PET scan. Qualitative analysis generally does not provide concentrations of FDG in regions of interest. Instead, differences are shown visually in varying degrees of color change.

Semi-quantitative PET-scans may provide a quantitative FDG uptake comparison between the region of interest and a reference region. In some cases, comparison of a reference region and a region of interest is defined as the Standardized Uptake Value (SUV). In some cases, SUV may be defined as the FDG uptake in the region of interest (e.g., a tumor or collection of rapidly metabolizing cells) compared to a uniform distribution of FDG throughout the entire body. In these embodiments, SUV values may depend on factors such as acquisition time (which is generally 60 minutes post FDG injection), blood glucose levels, and insulin levels. Since this method is quantitative, healthcare providers typically need to determine SUV cut-off values in order to determine whether a tissue is, for example, cancerous (or metabolically hyperactive, etc.) or benign. In general a cut-off value between 2-3 is commonly used. While semi-quantitative PET-scans that utilize SUV measurements provide more information than qualitative PET-scans, they tend to fail to provide the healthcare provider with absolute concentrations of FDG in regions of interest.

Quantitative PET allows the healthcare worker to determine the metabolic rate of glucose or metabolic rate of FDG in a region of interest. In most cases, quantitative PET is time consuming and computationally expensive, but provides real-time data and concentrations of FDG uptake within a region of interest of the patient. In general, two pieces of information aid in performing a quantitative PET-scan: multiple PET-scans of the region of interest performed over a period of time; and FDG concentration measurements in the blood. These two data points can be input into kinetic compartmental models to determine the uptake rate of glucose or FDG into the region of interest over a period of time. Quantitative PET-scan can be further broken down into Simplified Kinetic Analyses or Full Kinetic Analysis. In general, the differences between these two methods are the number of blood samples taken and the number of PET-scans obtained over time. As can be appreciated, the greater the number of PET-scans and blood samples taken within the desired period of time improves the accuracy of the glucose and FDG uptake values determined from the models.

Boron Neutron Capture Therapy:

Boron Neutron Capture Therapy (BNCT) generally comprises introducing a boron-containing compound into a patient, allowing that boron-containing compound to accumulate in a location of interest, and then directing a neutron beam at the location of interest. First, a compound comprising boron is injected into the patient and allowed to preferentially accumulate in a location of interest, such as a target tissue, over a period of time. After accumulation of the boron containing molecule, a neutron beam is directed at the location of interest. In various aspects, the neutron beam is directed at a diseased tissue or cell, for example a cancerous tumor. In most cases of BNCT, neutrons pass through normal tissue and cells containing little or no boron. There is thus little to no damage inflicted upon such cells and tissues by BNCT. In contrast, where neutrons are directed to cells or tissues containing large amounts of boron, the neutrons react with the boron to release various forms of radiation, most notably alpha particles. These alpha particles and other forms of ionizing radiation damage cells, structures, and compounds within the tissues (e.g., DNA, RNA, proteins, and the like). In some embodiments, the ionizing radiation results in cell death.

Epithermal neutrons are generally low energy neutrons that penetrate tissues with little or no interaction. However, epithermal neutrons strongly interact with boron. When a neutron collides with a boron atom, it yields an alpha particle. Alpha particles are the most biologically toxic form of ionizing radiation. Consequently, when a boron molecule is located within a cell and a neutron collides with it, the released alpha particle is free to cause damage to the vital structures and/or molecules within the cell, and may, in some cases, lead to cell death. Traditionally, in clinical settings two molecules have been used as the boron-containing compound in BNCT: boronophenylalanine (BPA) and sodium borocaptate (BSH). However, these molecules do not accumulate to significant amounts in cancer tissue as compared to non-cancer tissue. This is problematic for the use of BNCT, which requires boron concentrations to be sufficiently high in a tumor tissue (or other, highly metabolically active cell type) so as to deliver enough alpha particle radiation to damage the tumor, with minimal tissue toxicity in normal, neighboring tissues.

Epithermal neutrons preferentially interact with boron because boron has a high capture cross section for neutrons. Boron's capture cross section is significantly greater than other atoms that may accumulate in biological tissue. Consequently, the neutrons pass relatively freely through normal biological tissue and typically only interact with boron. When boron accumulates preferentially in diseased cells, BNCT may be used to target and treat the diseased cell. In some embodiments, approximately 20-35 micrograms of boron per gram of tissue may be used to treat a diseased tissue.

When non-radioactive boron (boron-10 or $^{10}B$) interacts with the epithermal neutron, the boron atom captures the neutron to change to an excited, or radioactive, form of $^{11}B$. The excited form of $^{11}B$ then decays, undergoing a fission reaction to release two high energy ions, $^{4}He^{2+}$ (alpha particle) and $^{7}Li^{3+}$ (lithium particle), and a low energy γ-ray. The alpha particle and lithium particle, in most cases, deliver the most biological toxic effect to the local tissue/cells. In most embodiments, the alpha particle and lithium particle have enough energy to travel approximately 10 micrometers before releasing all of their energy. Because most cells are on the order of 10 micrometers, the vast majority of the cytotoxic effect of the BNCT reaction occurs within or near the target cell. In addition to the radiation released from the boron-neutron reaction, various other forms of radiation contribute to the overall dose received by the tissue, however these other forms of radiation do not comprise the majority of the radiation dose, which comes from the boron-neutron reaction.

The cellular toxicity of the alpha particle is derived from its high mean energy deposition (high linear energy transfer (LET)) over a relatively short length (5-10 micrometers). In many cases, cytocidal effects of alpha particles do not depend on dose fractionation, dose rate, or hypoxia. In most embodiments, the cytocidal effect of the alpha particle is the result of DNA damage caused by the alpha particle. In most cases, an alpha particle traversing the nucleus of a cell results in cell death. Cellular death can be from one of many mechanisms, including apoptosis, autophagy, necrosis, and/or mitotic catastrophe.

Neutron Source and Neutron Dose (Dosimetry) for Boron Neutron Capture Therapy

While various neutron sources or neutron generators exist, including fission based reactor facilities, accelerator based reactor facilities, and other, more compact sources, fission based reactor facilities have been traditionally used for BNCT. The goal of the neutron source is to create a uniform distribution of low energy neutrons (thermal) in a targeted treatment volume. In various aspects, the neutron dose is capable of penetrating about 9 cm of tissue. In some embodiments, the neutron dose can be tailored to the boron concentration within the tissue. In some embodiments, for therapeutic use, neutrons are directed at a tissue containing boron at a level of between about 18-65 micrograms of boron per gram of tissue. Table 1 provides one example of some characteristics of the neutron dose and source according to at least one embodiment of the present disclosure. In some embodiments, treatment times may be extended when the neutron intensity is decreased, the concentration of boron is low, or if the target tissue is deeper than about 9 cm.

TABLE I

| Characteristic | Approximate Neutron Performance |
| --- | --- |
| Neutron and Photon Beam Contamination | $<2 \times 10^{-12}$ Gy cm$^2$ |
| Energy | $\sim 0.4$ eV $< E <\sim 10$-$20$ keV |
| Intensity, epithermal neutron flux | $>2 \times 10^9$ n cm$^{-2}$ s$^{-1}$ |
| Treatment time | $\sim 10$ min |

While nuclear reactors are the most widely used source of neutrons for BNCT, they are generally too large and expensive for wide spread use in hospitals. In some embodiments, smaller and less expensive neutron sources may be used. The accelerator based neutron source is an attractive neutron generator. In addition to accelerators, researchers are developing even more compact neutron generators at substantially lower cost that can be used in BNCT. One example is the D-D neutron generator that has been installed in Turin, Italy. Also the RF-Driven plasma source for neutron production being developed at Lawrence Berkeley National Laboratory maybe a future source of neutrons for BNCT.

Boronated Glucose and Fluorinated Glucose Doses:

In most embodiments, FDG and boronated glucose (BDG) are administered to the patient such that both forms of glucose are present in the patient simultaneously. In some embodiments, the two forms of glucose will transfer from the blood into the patient's tissues and cells. The amount of FDG and BDG administered to the patient can vary. In many embodiments, the amount of FDG and BDG administered to the patient and circulating in the bloodstream can be modified to optimize uptake and accumulation BDG at the target tissue. In some embodiments, two different methods of administering FDG and BDG to a patient may be used. In some embodiments, the FDG is administered to the patient prior to administration of the BDG. In some embodiments, the FDG is administered to the patient subsequent to administration of the BDG. In some embodiments, the FDG and the BDG are administered to the patent at the same time, via separate methods of administration. In some embodiments, the FDG and the BDG are co-administered to the patient.

Glucose may be modified to include boron at various locations on the glucose backbone, for example any one or more of the 1', 2', 3', 4', or 6' carbons may be bound to one or more boron molecules, which may be in the form of borane or boronic acid. In some embodiments, the 2' carbon of a glucose molecule has a boron substituent in place of the hydroxyl group. In these embodiments, which are depicted below as Formula I and Formula II, the 2' boron substituent is either bound to two hydrogens, such that it is a 2' borane substituent (Formula I), or two hydroxyl moieties, such that it is a boronic acid substituent (Formula II). In some embodiments, the 2' boron substituent is bound to a single hydrogen atom and a hydroxyl moiety. The structure of FDG is also depicted below, as Formula III.

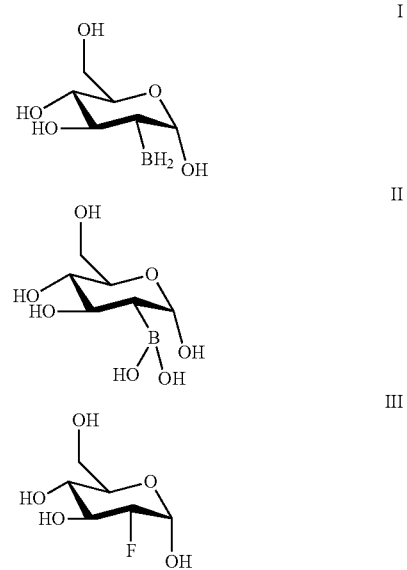

In some embodiments, FDG and BDG ware continuously injected into the blood stream such that the concentration of FDG and BDG are administered to the patient in steady-state amounts. The actual amount of FDG and BDG required for treatment of any particular patient will depend upon a variety of factors including: the disorder being treated and its severity; the specific FDG and/or BDG composition employed; the age, body weight, general health, sex and diet of the patient; the mode of administration; the time of administration; the route of administration; the presence of any one or more drugs used in combination or coincidental with the FDG and/or BDG; and the discretion of the prescribing physician. Delivering a certain amount of FDG and BDG will create blood that comprises FDG, BDG, and native glucose. The sum of the relative concentrations of each represents the total amount of glucose analog/native glucose in the blood. Given a particular cellular disorder (e.g., a tumor) and normal tissue uptake rate and the total concentration of BDG needed to obtain a therapeutic effect in the tumor and non-therapeutic effect in the normal tissue, in some embodiments it is desirable to allow the target tissue uptake these three components for the period of time necessary to achieve a therapeutic concentration of BDG in the target tissue but not in normal tissue. In some embodiments, the accumulation of modified glucose, in the form of FDG, is tracked with PET scan in order to predict the BDG concentration in both the target tissue and normal/surrounding tissue. The BDG concentration will correlate with the amount of FDG in the target tissue such that the amount of BDG present in the target tissue will approximate the amount of FDG present. Quantitation of FDG in the target tissue and in other tissues is thus a means of approximating the amount of BDG present.

In other embodiments, one or more bolus doses of FDG and BDG may be injected throughout the procedure to attain a FDG, BDG, and native glucose concentration within the blood stream that, while not constant, may still deliver the appropriate amount of BDG to the target tissue. In such embodiments, the accumulation of modified glucose is tracked with PET scan in order to predict and/or approximate the BDG concentration in both the target tissue and normal/surrounding tissues.

Dosing

In many embodiments, the dosage of FDG may be calculated based on activity of the radiolabelled fluorine. For example, a standard dose of FDG may be between about 370-185 MBq (Mega Becquerel) per 70 kg, or between about 6 and 2.5 MBq/kg. In various aspects, the amount of FDG will be less than about 60 MBq/kg and greater than about 0.25 MBq/kg.

In many embodiments, the dosage of BDG may be calculated from an initial PET scan using only FDG. The initial PET scan, performed after injecting a known concentration of FDG into the patient, will determine the concentration of FDG in both the target tissue and the normal surrounding tissue. From the known FDG concentrations in these two tissues, the known concentration of FDG administered, and the known therapeutic threshold of BDG in tissue, the therapeutic dose of BDG can then be calculated to ensure the maximal therapeutic dose of BDG in the target tissue while keeping the normal tissue below the therapeutic dose. The patient is then given BDG at the proper amount and concentration to achieve a therapeutic dose. For example, a standard dose of BDG may be between about 10 and 1 mg or boronated glucose per kg (weight of the patient). In most cases, the amount of BDG will be less than about 400 mg/kg and greater than about 0.04 mg/kg, or less than about 100 mg/kg and greater than about 0.1 mg/kg. The correct dose of BDG and the standard or similar concentration of FDG used in the first PET scan are delivered to the patient. Here the patient is given both the FDG and BDG together so that the FDG can be used with a second PET scan to confirm the therapeutic level of BDG in the tumor and non-therapeutic level within the normal surrounding tissue. It will be appreciated, however, that in some embodiments the first PET scan of FDG alone is sufficient to approximate the correct dose of BDG, such that BDG alone can be injected, without additional FDG. After the therapeutic levels are confirmed, the patient will be exposed to neutrons at the region of interested to destroy the cells in the target tissue and save, or minimize the amount of damage inflicted upon, the normal tissue. Hence the dose of both FDG and BDG is crucial to the safety and efficacy of the treatment.

Diseases

The presently disclosed methods, processes, devices, and/or compositions can be used to treat a wide variety of diseased cells that may metabolize and/or internalize more glucose than other cells. Cancer represents one type of disease that may, in some cases, be characterized by an increased glucose uptake and/or an increased cellular metabolism, various other diseases may also be characterized, in part, by an increased glucose uptake and/or metabolism, and may therefore be treatable by the presently claimed compositions and methods.

Many current treatments for diseases characterized by increased cellular uptake and metabolism of glucose (for example, cancer) may be harmful to normal tissue and cells and thus trigger unwanted side effects or adverse events. In the case of cancer, chemotherapy may adversely affect non-cancer cells such as hair follicle cells, red blood cells, white blood cells, etc. The presently disclosed methods, processes, and compositions may aid in treating these conditions without significantly affecting surrounding/normal tissue and cells. This may aid in reducing poor patient outcomes, unwanted side effects and/or adverse events.

In many cases, the disclosed methods, processes, devices, and compositions may affect tissue and cells that are not diseased, for example cells and tissue surrounding the diseased tissues and cells. In many embodiments, cells and tissue surrounding diseased tissues will accumulate less boron within the cells and may therefore accumulate less damage from alpha particle emissions.

The disclosed methods, processes, devices, and compositions may aid in the treatment of lung cancer. Cancerous lung tissue is known to internalize and metabolize substantially more glucose than surrounding, normal tissue. The etiology of the disease varies by stage. In early stage cancer, diseased lung tissue is relatively localized, whereas in later stages, diseased lung tissue is seen at metastatic sites. In some embodiments, the lung cancer is non-small cell lung cancer (NSCLC), small cell lung cancer, or any other variety of cancer originated from lung tissue. In some embodiments, the lung cancer is localized or at an early stage and located at, around, or in the mediastinum. Organs of the mediastinum typically display a lower level of glucose uptake than many other organs within the body. In many cases, normal lung tissue also has low avidity for glucose. In some cases, heart tissue and cells display variability in glucose uptake and use. In these cases, it may be useful to avoid directing epithermal neutrons toward heart tissue. In some embodiments, lung cancer patients may be treated with the present methods, processes, devices, and compositions wherein the heart tissue displays consistent and low glucose uptake and/or metabolism. In some cases, existing methods may aid in reducing the variability and amount of glucose in specific tissues, for example the use of ketogenic diets and fasting. In some embodiments, non-small cell lung cancer (NSCLC) may be treated. In some cases, the NSCLC is referred to as locally advanced non-small cell lung cancer, which may be characterized by localized and non-metastasized disease. In some cases, glucose uptake in NSCLC may act as a biomarker for disease progression, where lower glucose uptake indicates better long-term survival and recurrence rates.

Breast Cancer may also be treated by the presently disclosed methods, processes, devices, and compositions. In some embodiments the level of glucose uptake and metabolism may vary between subtypes of breast cancer. In many embodiments, breast cancer tumors, cells, and tissues display enhanced glucose uptake and metabolism compared with non-cancer cells and tissue. Other diseases may also be treated with the presently disclosed methods, processes, devices, and compositions, including, without limitation, skin cancer, prostate cancer, colorectal cancer, kidney cancer, bladder cancer, non-Hodgkin's lymphoma, endometrial cancer, thyroid cancer, pancreatic cancer, leukemia cancer, and ovarian cancer.

Melanoma is a form of skin cancer that originates from melanocytes, is the most deadly form of skin cancer, and the fifth most common type of cancer in the US (DUNKI-JACOBS, E. M.; CALLENDER, G. G.; MCMASTERS, K. M., 2013). Melanoma displays an increased glucose uptake as compared to normal tissue and consequently may be a candidate for treatment by the disclosed methods and compositions (DANIELSEN, M. et al, 2013).

Prostate Cancer may be treated by the disclosed methods and compositions. While most prostate cancers are generally slow growing and do not have a great avidity for glucose metabolism, there are a subset of prostate cancers which are poorly differentiated and display a high glucose metabolism in comparison to non-special type (NST) cancers (JADVAR, H., 2013; 2013). Consequently, methods provided by the present disclosure may be able to treat this highly glucose avid subset of prostate cancer patients.

Colorectal cancer may be treated by the disclosed methods and compositions. Colorectal carcinoma is the third most frequent form and third most deadly form of cancer in the US (BEN-HAIM, S.; ELL, P., 2009). Colorectal cancer is diagnosed, staged, and predicts outcomes of treatment by PET scans utilizing FDG because colorectal cancer displays increased glucose uptake as demonstrated by SUV values at around 8 (Ibid; ZERIZER, I. et al, 2012).

Kidney cancer may be treated by the disclosed methods and compositions. The vast majority of patients with kidney cancer present with renal cell carcinoma, which demonstrates an increased glucose uptake evident by SUV values greater than normal tissue (FERDA, J. et al, 2013). The main challenge with cancer within the kidney is that the kidney will typically display increased glucose uptake during performance of the disclosed methods because the FDG and boronated glucose analog will be filtered through the kidney. Consequently it may be difficult to treat renal cell carcinoma within the kidney or any other type of cancer located within the kidney (Ibid). However, it may be possible to wait longer before initiating treatment and/or before the performance of a PET scan, which may result in significant FDG and boronated glucose uptake in the cancer tissue and not nearly as much in the kidney's NST (SCHILLACI, O., 2012).

Bladder cancer may be treated by the disclosed methods and compositions. Bladder cancer is staged and diagnosed with PET scans and bladder cancer has demonstrated SUV values of ~7 after dual point PET scans (MERTENS, L. S. et al, 2012). While bladder cancer may be difficult to treat because large quantities of FDG and boronated glucose may be present in the bladder, bladder flushing, increased hydration, diuretic administration, and waiting longer times till treatment may enable the disclosed methods to be used on bladder cancer (Ibid). If bladder cancer metastasizes to other locations in the body, it may also be treated with the disclosed methods if NST does not possess excessive glucose uptake.

Lymphoma may be treated by the disclosed methods and compositions. Lymphomas consist of a variety of subtypes and can be broadly categorized as Hodgkins Lymphoma and Non-Hodgkins Lymphoma. Both types possess glucose avidity as evidenced by the high sensitivity and specificity of PET scans for both of these diseases (KOSTAKOGLU, L.; CHESON, B. D., 2013). Additionally PET scans and SUV after treatment correlate with treatment response and outcomes, where a lower SUV after treatment or a complete metabolic response indicate better treatment outcome than higher SUV or partial metabolic treatment response (Ibid).

Endometrial Cancer may be treated by the disclosed methods and compositions. Endometrial cancer is a common gynecological cancer and PET has demonstrated utility in staging and diagnosing endometrial cancer because of its avidity for FDG and glucose (KADKHODAYAN, S. et al, 2013). Consequently the disclosed methods may be useful for treatment of endometrial cancer because it displays and avidity for FDG and glucose.

Thyroid Cancer may be treated by the disclosed methods and compositions. Thyroid tumors are by far the most common form of endocrine tumor and are increasing in prevalence. Also thyroid tumors, especially aggressive forms of such tumors, display an increased glucose metabolism in comparison to normal tissue as evidenced by PET scans of thyroid tumors (TREGLIA, G. et al, 2013). Consequently the disclosed methods may be able to treat thyroid tumors that express a substantially greater amount of glucose than NST.

Pancreatic Cancer may be treated by the disclosed methods and compositions. Pancreatic cancer displays focal uptake or high levels of FDG uptake with PET scans and PET is currently used to help diagnose pancreatic cancer and differentiate it from pancreatitis (DIBBLE, E. H. et al, 2012). Additionally pancreatic cancer often presents as a surgically unresectable disease (Ibid). Consequently, the increased glucose uptake of pancreatic cancer in comparison to NST and the fact that many pancreatic tumors cannot be surgically removed, makes pancreatic cancer a disease than can possibly be treated with the disclosed methods.

Ovarian Cancer may be treated by the disclosed methods and compositions. Ovarian cancer is the most deadly form of gynecological cancer and malignant ovarian cancers display intense FDG uptake as evidenced on PET scans (KITAJIMA, K. et al, 2011). Consequently the disclosed methods may be used to treat ovarian cancers than display this increased glucose uptake than NST.

Cervical cancer may also be treated by the disclosed methods and compositions. Cervical carcinoma is one of the most common and deadly cancers for women. Most cervical cancers display and avidity for FDG and consequently may be treated by the disclosed methods (PATEL, C. N. et al, 2011).

Head and Neck cancers may also be treated by the disclosed methods and compositions. Head and neck cancers are a heterogeneous class of diseases that display an increased glucose uptake as evidenced by the SUV of these diseases on PET scans (CASTALDI, P. et al, 2012). Additionally a complete response in metabolic rate of FDG after treatment of head and neck cancers correlates with improved outcomes in comparison to non- or partial metabolic responders (Ibid). Consequently by targeting a treatment directly at the metabolically active regions of the head and neck tumors with boronated glucose, the disclosed methods may not only be able to treat many head and neck cancers, but significantly improve the prognosis over current treatments.

Mesothelioma Cancer may be treated by the disclosed methods and compositions. Since mesothelioma displays and increased glucose uptake than NST as evidenced by PET scans and complete metabolic responders to treatment demonstrated superior outcomes than non- or partial metabolic responders as measured by and FDG PET scan (TSUTANI, Y. et al, 2013), the disclosed methods may be able to treat mesothelioma patients and improve outcomes.

Inflammatory diseases may be treated by the disclosed methods and compositions. Inappropriate inflammatory reactions and slow resolution of inflammation poses serious side effects for nearby healthy tissue (WU, C. et al, 2013). Inflammation can be initiated by infectious agents or without infection agents (sterile inflammation). Many diseases are thought to be caused by sterile inflammation. Inflammation can be detected by PET scans utilizing FDG because inflammatory cells possess an increased glucose uptake than NST. Consequently a variety of inflammatory conditions may be treated by the disclosed methods including but not limited to atherosclerosis, arthritis, stroke, many autoimmune diseases, vasculitis, valvular information, skin inflammation, bone inflammation, myocardial inflammation, cystic fibrosis, and sarcoidosis (SOBIC-SARANOVIC, D. et al, 2012).

Polycystic kidney disease may be treated by the disclosed methods and compositions. Polycystic kidney disease is a relatively common genetic disease that causes cysts to form from renal tubule cells and eventually causes End-Stage Renal Disease (ROWE, I. et al, 2013). Currently there are no treatments for polycystic kidney disease and recent data indicate that the cells that form the cysts possess an increased glucose uptake as compared to normal tissue and perform aerobic glycolysis.

REFERENCES

Neutron Capture Therapy, Principles and Applications, Springer-Verlag Press, W. A. G. Sauerwein, A. Wittig, R. Moss, and Y. Nakagawa, eds., 2012.

TJARKS, W., et al, Synthesis and in Vitro Evaluation of Boronated Uridine and Glucose Derivatives for Boron Neutron Capture Therapy, J. Med. Chem., 35, 1628-1633, 1992.

PASS H, Carbone D, Johnson D, Minna J, Scagliotti G, Turrisi A. Principles and Practice of Lung Cancer: The Official Reference Text of the International Association for the Study of Lung Cancer (IASLC). Philadelphia, Pa.: Lippincott Williams & Wilkins. 2010.

FUKUCHI, K et al. Benign variations and incidental abnormalities of myocardial FDG uptake in the fasting state as encountered during routine oncology positron emission tomography studies. The British journal of radiology, England, v. 80, n. 949, 3-11, January 2007.

KHAN A(A), Sarika, Bhattcharya A, Singh B, Mittal BR. CAD 1 (ORAL): Variability of F18-FDG uptake in myocardium. Indian Journal of Nuclear Medicine, v. 25, n. 3, 103-108, 2010.

WANG, Yingbing et al. Standardized uptake value atlas: characterization of physiological 2-deoxy-2-[18F]fluoro-D-glucose uptake in normal tissues. Molecular imaging and biology: MIB: the official publication of the Academy of Molecular Imaging, United States, v. 9, n. 2, 83-90, 2007.

WILLIAMS, Gethin; KOLODNY, Gerald M. Suppression of Myocardial 18F-FDG Uptake by Preparing Patients with a High-Fat, Low-Carbohydrate Diet. AJR. American journal of roentgenology, v. 190, n. 2, W151-W156, February 2008.

SCHILLACI, Orazio. Use of dual-point fluorodeoxyglucose imaging to enhance sensitivity and specificity. Seminars in nuclear medicine, United States, v. 42, n. 4, 267-80, July 2012.

GOVINDAN, Ramaswamy; BOGART, Jeffrey; VOKES, Everett E. Locally advanced non-small cell lung cancer: the past, present, and future. Journal of thoracic oncology: official publication of the International Association for the Study of Lung Cancer, United States, v. 3, n. 8, 917-28, August 2008.

MOLINA, Julian R et al. Non-small cell lung cancer: epidemiology, risk factors, treatment, and survivorship. Mayo Clinic proceedings, United States, v. 83, n. 5, 584-94, May 2008.

VIDETIC, Gregory G. M. Locally advanced non-small cell lung cancer: what is the optimal concurrent chemoradiation regimen? Cleveland Clinic journal of medicine, United States, v. 79 Electronic Suppl 1, eS32-7, May 2012.

CHOI, Noah C et al. Potential of 18F-FDG PET toward personalized radiotherapy or chemoradiotherapy in lung cancer. European journal of nuclear medicine and molecular imaging, Germany, v. 40, n. 6, 832-41, June 2013.

ESCHMANN, Susanne Martina et al. 18F-FDG PET for assessment of therapy response and preoperative re-evaluation after neoadjuvant radio-chemotherapy in stage III non-small cell lung cancer. European journal of nuclear medicine and molecular imaging, v. 34, n. 4, 463-471, March 2007.

MASSACCESI, Mariangela et al. $^{18}$F-FDG PET-CT during chemo-radiotherapy in patients with non-small cell lung cancer: the early metabolic response correlates with the delivered radiation dose. Radiation oncology (London, England), England, v. 7, p. 106, 2012.

HELLWIG, Dirk et al. Value of F-18-fluorodeoxyglucose positron emission tomography after induction therapy of locally advanced bronchogenic carcinoma. The Journal of thoracic and cardiovascular surgery, United States, v. 128, n. 6, 892-9, December 2004.

BARTH, Rolf F et al. Current status of boron neutron capture therapy of high grade gliomas and recurrent head and neck cancer. Radiation oncology (London, England), England, v. 7, p. 146, 2012.

GROHEUX, David et al. Correlation of high 18F-FDG uptake to clinical, pathological and biological prognostic factors in breast cancer. European journal of nuclear medicine and molecular imaging, Germany, v. 38, n. 3, 426-35, March 2011.

GROHEUX, David et al. Prognostic impact of (18)FDG-PET-CT findings in clinical stage III and IIB breast cancer. Journal of the National Cancer Institute, United States, v. 104, n. 24, 1879-87, December 2012.

YALCIN, B. Overview on locally advanced breast cancer: defining, epidemiology, and overview on neoadjuvant therapy. Experimental oncology, Ukraine, v. 35, n. 4, 250-2, December 2013.

OZKAN, E. Positron emission tomography/computed tomography in locally advanced breast cancer. Experimental oncology, Ukraine, v. 35, n. 4, 253-7, December 2013.

DUNKI-JACOBS, Erik M; CALLENDER, Glenda G; MCMASTERS, Kelly M. Current management of melanoma. Current problems in surgery, United States, v. 50, n. 8, 351-82, August 2013.

DANIELSEN, Maria et al. Positron emission tomography in the follow-up of cutaneous malignant melanoma patients: a systematic review. American journal of nuclear medicine and molecular imaging, v. 4, n. 1, 17-28, 2013.

JADVAR, Hossein. Imaging evaluation of prostate cancer with 18F-fluorodeoxyglucose PET/CT: utility and limitations. European journal of nuclear medicine and molecular imaging, v. 40, n. S1, 5-10, July 2013.

JADVAR, Hossein. Molecular Imaging of Prostate Cancer with PET. Journal of Nuclear Medicine, v. 54, n. 10, 1685-1688, October 2013.

BEN-HAIM, Simona; ELL, Peter. 18F-FDG PET and PET/CT in the evaluation of cancer treatment response. Journal of nuclear medicine: official publication, Society of Nuclear Medicine, United States, v. 50, n. 1, 88-99, January 2009.

ZERIZER, I et al. The role of early 18F-FDG PET/CT in prediction of progression-free survival after 90Y radio-embolization: comparison with RECIST and tumour density criteria. European journal of nuclear medicine and molecular imaging, v. 39, n. 9, 1391-1399, September 2012.

FERDA, Jiri et al. 18F-FDG-PET/CT in potentially advanced renal cell carcinoma: a role in treatment decisions and prognosis estimation. Anticancer research, Greece, v. 33, n. 6, 2665-72, June 2013.

MERTENS, Laura S et al. Detecting primary bladder cancer using delayed (18)F-2-fluoro-2-deoxy-D-glucose-positron emission tomography/computed tomography imaging after forced diuresis. Indian journal of nuclear medicine: IJNM: the official journal of the Society of Nuclear Medicine, India, India, v. 27, n. 3, 145-50, July 2012.

KOSTAKOGLU, Lale; CHESON, Bruce D. State-of-the-Art Research on "Lymphomas: Role of Molecular Imaging for Staging, Prognostic Evaluation, and Treatment Response". Frontiers in oncology, v. 3, 2013.

KADKHODAYAN, Sima et al. Accuracy of 18-F-FDG PET imaging in the follow up of endometrial cancer patients: systematic review and meta-analysis of the literature. Gynecologic oncology, United States, v. 128, n. 2, 397-404, February 2013.

TREGLIA, Giorgio et al. The role of positron emission tomography and positron emission tomography/computed tomography in thyroid tumours: an overview. European archives of oto-rhino-laryngology: official journal of the European Federation of Oto-Rhino-Laryngological Societies (EUFOS): affiliated with the German Society for Oto-Rhino-Laryngology-Head and Neck Surgery, Germany, v. 270, n. 6, 1783-7, May 2013.

DIBBLE, Elizabeth H et al. PET/CT of cancer patients: part 1, pancreatic neoplasms. AJR. American journal of roentgenology, United States, v. 199, n. 5, 952-67, November 2012.

KITAJIMA, Kazuhiro et al. Spectrum of fluorodeoxyglucose-positron emission tomography/computed tomography and magnetic resonance imaging findings of ovarian tumors. Japanese journal of radiology, Japan, v. 29, n. 9, 605-8, November 2011.

PATEL, Chirag N et al. 18F-FDG PET/CT of cervical carcinoma. AJR. American journal of roentgenology, United States, v. 196, n. 5, 1225-33, May 2011.

CASTALDI, Paola et al. Can "early" and "late" 18F-FDG PET-CT be used as prognostic factors for the clinical outcome of patients with locally advanced head and neck cancer treated with radio-chemotherapy? Radiotherapy and oncology: journal of the European Society for Therapeutic Radiology and Oncology, Ireland, v. 103, n. 1, 63-8, April 2012.

TSUTANI, Y et al. Prognostic significance of metabolic response by positron emission tomography after neoadjuvant chemotherapy for resectable malignant pleural mesothelioma. Annals of oncology: official journal of the European Society for Medical Oncology/ESMO, England, v. 24, n. 4, 1005-10, April 2013.

Akan Z, Turkmen M, Cakir T, Reyhancan I A, Colak Ü, Okka M, Kizdtas S. Modification of the radial beam port of ITU TRIGA mark II research reactor for BNCT applications. Appl Radiat Isot 2015, May; 99:110-6.

Akan Z Boron neutron capture therapy for breast cancer. International Journal of Women's Health and Reproduction Sciences 2015, February 7; 3(2):77.

Zafer Akan Complexion of boric acid with 2-deoxy-d-glucose (DG) as a novel boron carrier for BNCT. Medical Science and Discovery 2014, October; Vol 1:65-71.

Akan Zafer. Genotoxicity and cytotoxicity of novel 10B carrier ((2R)-4,5,6-trihydroxy-2-2(hydroxymethyl)tetra-hydro-2hpyran-3-yl)boronic acid). Medical Science and Discovery 2014, December; Vol 1 (No 4):96-108.

Witczak Zbigniew, Fischer Frederick. Compositions of pharmaceuticals for use in low energy neutron therapy. United States Patent Application Publication February 2008. Publication Number US 2008/0050309 A1.

EXAMPLES

The following examples describe in detail certain embodiments of the compositions and methods disclosed herein. It will be apparent to those skilled in the art that many modifications, both to materials and methods, may be practiced without departing from the scope of the disclosure.

Example 1—Research Plan

Preclinical—In Vitro:
Production and Analysis of Various Boronated Glucose Molecules Boronated glucose molecules are synthesized by standard organic chemistry techniques utilizing boron-10. The boronated glucose molecules are enriched for boron-10 while molecules containing boron-11 and/or other isotopes are discarded. The boronated glucose is then analyzed by HPLC to determine purity and confirm identity. Boronated glucose molecules are lyophilized and stored in a sealed container away from exposure to UV light and moisture. When stored in this manner at room temperature (15-20° C.) protected from light and moisture, the boronated glucose molecules are stable up to 31 days.

In one embodiment, boronated glucose is synthesized by a low to high pH reaction of boronic acid and 2-deoxy glucose. Briefly, a first solution of 0.1 M concentration of boronic acid and 0.5 M concentration of Tiron is prepared in distilled water and incubated for about one hour at about pH 3 and about 50° C. A second solution of 0.1 M concentration of boronic acid and 0.5 M concentration of 2-deoxy glucose is prepared in distilled water and incubated for about one hour at about pH 3 and about 50° C. The first and second solutions are then combined, mixed, and incubated at pH 3 for about 1 hour. The pH of the solution is then gradually increased from about pH 3 to about pH 7. After the reaction, FTIR-ATR, HPLC, and LC-MS are performed to confirm the presence of a boronated glucose analog and determine purity and yield. Additional methods of boronated glucose synthesis are disclosed at Witczak et. al U.S. publication 2008/0050309, Akan et al. 2014, Akan et al. 2015, Akan et al. 2015, and Akan et al. 2014.

Different Formulations

Boronated glucose is dissolved into a sterile pharmaceutical grade sodium chloride solution. FDG is prepared in a similar manner Various concentrations of boronated glucose and FDG are used to achieve a final, desired concentration.

Methods for Determining Transport of Boronated Glucose Molecules (BGM) In Vitro

Cells are analyzed for their ability to internalize and metabolize boronated glucose. For example, uptake is studied via various glucose transporter pathways, especially glucose transporters that are up-regulated on cancer cells. Boronated glucose concentrations between 1000 mg/dL and 0.1 mg/dL are tested for cellular uptake and cytotoxicity.

Mutagenic Affect

The mutagenic effect of BGM and neutrons are analyzed by exposing cell lines to BGM. After removal of BGM solution, the cells are irradiated with neutrons. Cell survival is determined by the colony-formation assay and mutagenic impact is measured by the mutation frequency at the hypoxanthine-guanine phosphoribo-syltransferase (HPRT) locus.

Preclinical-Animal Model

A variety of animal models are used for preclinical animal testing of boronated glucose molecules (BGM) including mice, rats, rabbits, dogs, pigs, sheep, and monkeys. For animal model testing, BGM accumulation or retention in tissues outside the treatment area is shown to not affect survival of these cells or the therapeutic action.

Initial acute toxicity studies are used to determine the $LD_{50}$, or median lethal dose, of the disclosed technique by intraperitoneal injection and/or intravenous injection of various amounts of BGM into mice, for example between 3.5 g and 1 mg of BGM/kg. In addition to the total amount injected, the rate at which the BGM is injected is also studied. The cause and time of death, if any, is determined and recorded. Additionally, the effect on various organ systems is studied. In addition to single dose administration, multiple doses administered over various time points are studied to determine the toxicity on organ systems and death. Between one and sixteen doses over the course of up to eights hour will be administered to determine acute toxicity. Each dose will be between 3.5 g of BGM/kg and 1 mg of BGM/kg. In addition to multiple discrete doses, a continuous infusion of BGM over the course of up to 8 hours will be studied. The total amount of BGM delivered during continuous infusion will be between 3.5 g of BGM/kg and 1 mg of BGM/kg.

Long-term acute toxicity studies are performed over the course of at least 3 months to determine the long-term effect of various doses of BGM. Multiple doses (up to once daily) over the three-month period will be used. Each dose will be between 3.5 g of BGM/kg and 1 mg of BGM/kg.

Animal testing is also performed in order to assess pharmacokinetics (such as liver metabolism) and tissue distribution of BGM. The half-life of BGM in blood after intravenous and/or intraperitoneal injection is studied by monitoring the boron levels in blood. A two compartmental model is used. Plasma protein binding of BGM, especially BGM binding to albumin, is studied using nuclear magnetic resonance spectroscopy. It is useful to determine the protein bound and non-protein bound fraction of BGM in blood, as free BGM is more readily available for cellular uptake than that which is protein bound. Distribution and excretion of BGM after intravenous and intraperitoneal injection is studied by examining the boron content in urine over time and also determining the amount of boron in certain internal organs including, for example, the brain, kidneys, liver, and lung.

Boron Uptake Studies

The uptake ratio of BGM in tumors and normal tissue is analyzed by administering BGM and performing a quantitative kinetic PET scan. Additionally, the tumors and normal tissue are removed from the animal and analyzed for boron content. These uptake ratio studies determine the selectivity of BGM for various types of tumors and normal tissue. Various BGM doses and rates of dose administration are used to determine their effect on BGM uptake. Between one and sixteen doses over the course of up to eights hour will be administered to determine boron uptake. Each dose will be between 3.5 g of BGM/kg and 1 mg of BGM/kg. In addition to multiple discrete doses, a continuous infusion of BGM over the course of up to 8 hours will be studied. The total amount of BGM delivered during continuous infusion will be between 3.5 g of BGM/kg and 1 mg of BGM/kg. Boron uptake in, for example, lung tumors can also be studied. Pulmonary metastases are induced with DHD/K12/TRb colon-carcinoma cells obtained from 1,2dimethylhydrazine-induced colon adenocarcinoma in syn-geneic BDIX rats, selected and cloned for their capacity to induce progressive and metastatic tumors in the syngeneic host. DHD/K12/TRb cells are injected into the inferior vena cava of each rat to induce lung metastases. Ten days after lung tumor injection, BGM is administered to the rats at various concentrations and at various rates. Between one and sixteen doses over the course of up to eights hour will be administered to determine boron uptake. Each dose will be between 3.5 g of BGM/kg and 1 mg of BGM/kg. In addition to multiple discrete doses, a continuous infusion of BGM over the course of up to 8 hours will be studied. The total amount of BGM delivered during continuous infusion will be between 3.5 g of BGM/kg and 1 mg of BGM/kg. Two administration routes are studied: intra-peritoneal and intravenous infusion. The animals are then sacrificed using a lethal dose of general anesthesia at different time intervals after BPA administration (for example, at 1, 2, 4, 6 and 8 hours post-administration). For each time interval, at least 3 healthy rats and 3 rats bearing pulmonary metastases are treated. The lungs are explanted, frozen in liquid nitrogen and prepared for boron concentration analysis. Boron concentration in the tissues is evaluated using morphological analysis to determine the biological composition of the samples (healthy tissue, tumor, necrosis), neutron autoradiography to visualize macroscopic boron distribution imaging and a-spectrometry to measure the boron concentration values.

Boron Uptake and Neutron Irradiation Efficacy Studies in Rats

EMT6 cells are purchased from American Type Culture Collection and cultured in Weymouth medium supplemented with 10% FBS as recommended by American Type Culture Collection. After cells reach log-phase growth they are centrifuged and the cell pellets are re-suspended in PBS solution. For tumor induction, EMT6 cells are inoculated into the right flank of female BALB/c mice in the amount of about $1 \times 10^6$ cells/mouse. For bio-distribution studies of BGM, when the tumors reach a target volume of 80 to 150 $mm^3$, mice are administered BGM via tail vein injection, and the distribution of boron in blood and organs are evaluated at specific intervals after injection, for example every 5 minutes for up to 8 hours after injection, or every 15 minutes or 30 minutes. At each time point, brain, lung, heart, liver, kidney, spleen, tumor, blood, and tail samples are harvested and stored at −80° C. Tissues are digested by using a Microwave Accelerated Reaction System (Mars; CEM), and their boron content is determined via inductively coupled plasma optical emission spectroscopy (ICP-OES) with a PerkinElmer Optima 7000 DV.

For therapeutic effect studies, when tumors have reached the 80- to 150-$mm^3$ target volume, mice are administered BGM via tail-vein injections and subjected to thermal neutron irradiation. The effect of the neutron radiation on cells within the tumors that have taken up BGM is evaluated based on changes in tumor volume over time. Neutron-only tumor-bearing mice are given no boron compounds but are exposed to the same irradiation protocol as the treatment group. Control mice are neither injected with a boron agent nor exposed to thermal neutron irradiation. Tumors on all mice are measured at least once daily throughout the experiment. Tumor volumes are calculated and time-to-event curves are estimated using the Kaplan-Meier method and outcomes among treatment groups are compared by using the log-rank test. Biodistribution plots and growth curves are constructed, and survival analysis is conducted.

Clinical Studies

The BGM pharmacodynamics and pharmacokinetics are investigated in subtherapeutic and below expected toxic doses. Determination of the tumor to normal tissue BGM uptake ratio is also determined in this study. The ability of FDG to predict BGM transport by injecting BGM and FDG into the patient is determined. The FDG concentration in the tumor is first determined, then the tumor is resected to determine the concentration of BGM in the tumor and NST by gamma ray spectroscopy. While the doses of BGM injected are expected to be below toxic levels, these studies are also designed to determine any toxicity of the BGM doses. These studies yield no therapeutic affect for patients and less than 10 patients are used for Phase 0 exploratory clinical studies.

Phase I

Phase I consists of two separate studies and uses between 20-100 patients. The first phase (Phase I Part A) analyzes BGM at sub and then near-therapeutic dose of BGM, while the second phase (Phase I Part B) analyzes BGM and neutron irradiation at sub and then near-therapeutic doses.

Phase I Part A

Determine pharmacovigilence and tolerability of near-therapeutic doses of BGM in 20-100 patients. Determine BGM tolerability at near therapeutic doses and the uptake ratio between tumor and normal tissue. BGM is used alone (without irradiation) in this phase. Pharmacokinetic studies will be performed in order to properly determine when to apply the irradiation to a target tissue. Pharmacodynamic studies will also be performed in order to determine the biochemical and physiological effects of BGM on the body, to confirm the mechanisms of BGM action within the body and to obtain clinical data showing the relationship between BGM concentration within a target tissue and therapeutic effect. End points are pharmacokinetics and pharmacodynamics Pharmacokinetics indicate the timing and type of drug infusion and the timing for neutron irradiation.

Phase I Part B

Tolerability and safety of the combination of BGM and irradiation are first evaluated. Trials will begin with sub-therapeutic doses of both BGM and irradiation to determine tolerability at low levels, but will then increase both BGM dose and amount of irradiation administered to therapeutic or near-therapeutic levels to determine safety.

Phase II

These studies will be performed in order to determine if BGM displays clinical efficacy at the various therapeutic doses determined from Phase I. 50-300 patients are tested in order to explore the antitumor activity of the combination of BGM with neutron irradiation. Optimal dosing (concerning BGM and irradiation) and timing are studied with specificity. Trials are case series to test safety and activity of BNCT with BGM in selected groups of patients. Efficacy will be determined by metabolic response by performing a PET scan of the treated/target area 1-month post therapy. Shorter post-therapy times may also be utilized, depending on severity of the tumor, health of the patient and the discretion of the treating physician.

Phase III

Phase III clinical trials are randomized controlled multi-center trials designed to definitely determine the therapeutic effect of the BGM and neutron irradiation doses in comparison to the current treatment standard in a large group of patients (200-3,000 or more).

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A composition for the treatment of a cellular disorder, comprising:
   fluorinated glucose;
   boronated glucose, the boronated glucose comprising one or more boron molecules directly bound to one or more locations on a glucose backbone; and
   a pharmaceutically acceptable vehicle, adjuvant or excipient.

2. The composition of claim 1, wherein the fluorinated glucose and the boronated glucose are formulated for uptake into one or more cells.

3. The composition of claim 2, wherein the boronated glucose is formulated for contact with epithermal neutrons subsequent to the uptake into the one or more cells.

4. The composition of claim 1, wherein the cellular disorder is cancer.

5. The composition of claim 4, wherein the cancer is selected from non-small cell lung cancer, small cell lung cancer.

6. The composition of claim 1, wherein the boronated glucose is a compound of Formula (IV):

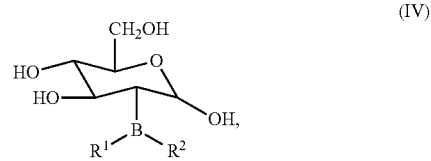

(IV)

wherein:
   R1 and R2 are independently selected from H, —OH and $C_{1-4}$ alkyl.

7. The composition of claim 1, wherein the fluorinated glucose is the following compound of Formula (III):

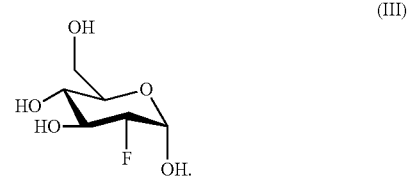

(III)

8. A method of treating a cellular disorder, comprising:
   administering fluorinated glucose to a subject;
   administering boronated glucose to the subject, wherein the boronated glucose comprises one or more boron molecules directly bound to one or more locations on a glucose backbone;

performing a PET scan of the subject;
identifying the locations of a target tissue from the PET scan, and
contacting the boronated glucose localized within the target tissue with epithermal neutrons;
wherein the fluorinated glucose and the boronated glucose co-localize to the same location in the subject.

9. The method of claim 8, wherein the fluorinated glucose is administrated prior to the boronated glucose.

10. The method of claim 8, wherein the fluorinated glucose is administrated subsequent to the boronated glucose.

11. The method of claim 8, further comprising, prior to performing the PET scan, allowing the boronated glucose and the fluorinated glucose to selectively accumulate in the target tissue.

12. The method of claim 8, wherein, upon contact with the epithermal neutrons, the boron in the boronated glucose releases a radioactive alpha particle.

* * * * *